US00PP22826P2

(12) United States Plant Patent
Egger

(10) Patent No.: US PP22,826 P2
(45) Date of Patent: Jun. 26, 2012

(54) ***SEDUM* PLANT NAMED 'BIRTHDAY PARTY'**

(50) Latin Name: ***Sedum* sp.**
Varietal Denomination: Birthday Party

(75) Inventor: Janet Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/930,852

(22) Filed: Jan. 19, 2011

(51) Int. Cl.
*A01H 5/00* (2006.01)

(52) U.S. Cl. ..... Plt./479

(58) Field of Classification Search ..... Plt./479
See application file for complete search history.

*Primary Examiner* — Kent L Bell
(74) *Attorney, Agent, or Firm* — Jondle & Associates, P.C.

(57) ABSTRACT

A new and distinct hybrid of *Sedum* plant substantially as shown and described, with deep red purple flowers in a large inflorescence, cut and dark leaf margins, new leaves that are glossy, yellow green tinted red brown with red margins, strongly upright stems, and a low, clumping habit.

1 Drawing Sheet

Botanical denomination: *Sedum* sp.

Variety designation: 'Birthday Party'.

Parentage: *Sedum telephium* dark leaf×*Sedum spectabile* 'Neon'.

Cross reference: *Sedum* 'Beach Party', applied for in copending U.S. Plant patent application Ser. No. 12/930,866.

The present invention relates to a new and distinct cultivar of *Sedum* and given the cultivar name of 'Birthday Party'. *Sedum* is in the family Crassulaceae. *Sedum* 'Birthday Party' originated from a cross between an unnamed, proprietary, and unpatented dark leaf *Sedum telephium* as the seed parent and *Sedum spectabile* 'Neon', unpatented, as the pollen parent.

Compared to the dark leaf *Sedum telephium* seed parent, the new cultivar is has much greener foliage and much larger inflorescences with darker flower color.

Compared to the pollen parent, *Sedum spectabile* 'Neon', the new cultivar has leaves that are glossier and tinted red brown on the margins rather than being glaucous and evenly yellow green.

Compared to *Sedum* 'Class Act' (U.S. Plant Pat. No. 20,125), the new variety is shorter with leaves that are darker and more cut on the margins. The flowers of the new variety are smaller in denser flatter inflorescences. The flowers of the new variety are a brighter red purple.

Compared to *Sedum* 'Mr. Goodbud' (U.S. Plant Pat. No. 17,671), the new variety is shorter with leaves that are darker and more cut on the margins. The flowers of the new variety are much darker.

Compared to *Sedum* 'Beach Party', a sibling applied for in copending U.S. Plant patent application Ser. No. 12/930,866, the new variety has much darker flower color.

This new and unique *Sedum* is distinguished by:

1. medium deep red purple flowers in large inflorescences,
2. cut and dark leaf margins,
3. new leaves that are glossy, yellow green tinted red brown with red margins,
4. strongly upright stems, and
5. a low, clumping habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 2 year old *Sedum* 'Birthday Party' growing in a 2 gallon container outside in May in Canby, Oreg.

FIG. 2 shows a 1 year old *Sedum* 'Birthday Party' growing in the trial field in September in Canby, Oreg.

DETAILED PLANT DESCRIPTION

The following is a detailed description of the new *Sedum* hybrid based on observations of two year old specimens grown in a garden in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:

*Type*.—Herbaceous perennial.
*Hardiness*.—USDA Zone 4 to 9.
*Size*.—13 cm tall from the ground to the base of the inflorescence and 44 cm wide.
*Habit*.—Erect, clumping.
*Vigor*.—Excellent.

Stem:

*Number*.—About 11.
*Size*.—13 cm long and 10 mm wide.
*Internode length*.—1 to 3 cm long.
*Color*.—Yellow Green 145A heavily tinted Greyed Purple 187B to Greyed Purple 187A at the base.
*Texture*.—Succulent.
*Surface*.—Glabrous and glossy.

Leaf:

*Type*.—Simple.

*Arrangement*.—Opposite.

*Shape*.—Elliptic to slightly obovate.

*Apex*.—Acute.

*Base*.—Cuneate.

*Venation*.—Pinnate.

*Margins*.—Irregularly deeply serrate.

*Blade size*.—Grows to 10.5 cm long and 5.8 cm wide.

*Surface*.—Glabrous, glossy when young on both sides.

*Texture*.—Thick, spongy, succulent.

*Petiole*.—Leaves sessile.

*Leaf color*.—Topside Green 137B edged and tinted with Greyed Purple 187A with the vein Yellow Green 147C; bottom side Green 147B edged and lightly tinted Greyed Purple 187A with the vein Yellow Green 147C.

Inflorescence:

*Type*.—Terminal, corymbose, umbel-like.

*Number of flowers*.—Over 1000 per stem (increases with age).

*Pedicels*.—1 to 3 mm long, 1 mm wide, glaucous, Brown N200C.

*Peduncle*.—17 cm tall and 4 to 6 mm wide, Greyed Green 193A tinged with Greyed Purple 187A, succulent, glabrous.

*Size*.—14 to 20 cm long and 14 to 20 cm wide.

*Bloom period*.—August through September in Canby, Oreg.

Flower bud:

*Size*.—2 mm wide, 5 mm deep.

*Description*.—Ovoid.

*Color*.—White 155A tinted Greyed Purple 187A darkening to Greyed Purple 187B at the tip.

Flower:

*Type*.—Complete, actinomorphic.

*Shape*.—Stellate.

*Size*.—6 mm deep and 12 mm wide.

*Color*.—Red Purple 64A.

*Corolla description*.—12 mm wide and 5 mm deep, 5 petals, each lanceolate, 6 mm long and 1.5 mm wide, margins entire, tip acuminate, glabrous on both sides, topside Red Purple 64A, bottom side Greyed Purple 186D.

*Calyx description*.—2.5 mm deep and 2.5 mm wide, campanulate, 5 lobes, divided to the base, margins entire, tip acute, glabrous, Greyed Orange 177B on both sides.

*Stamen description*.—10 in number, 4 mm long, filaments 3 mm long, Red Purple 64A, anthers Greyed Purple N186A, no pollen, male sterile.

*Pistil description*.—5 separate prominent carpels, each 6 mm deep and 1.5 mm wide, Red Purple 64A, style 2 mm long, Purple 77A, stigma rounded, Purple 77A.

*Fragrance*.—None.

*Lastingness*.—Each stem lasts up to a month.

Fruit:

*Type*.—Ventrally dehiscent follicle, erect, attenuate.

*Fertility*.—None.

*Color*.—Greyed Purple 187A at top and gray tan at bottom, Grey 200B.

Seed: No seed produced.

Disease and pest resistance or tolerance: Pest and disease resistance are typical for this type of *Sedum*.

I claim:

1. A new and distinct hybrid of *Sedum* plant as herein illustrated and described.

* * * * *

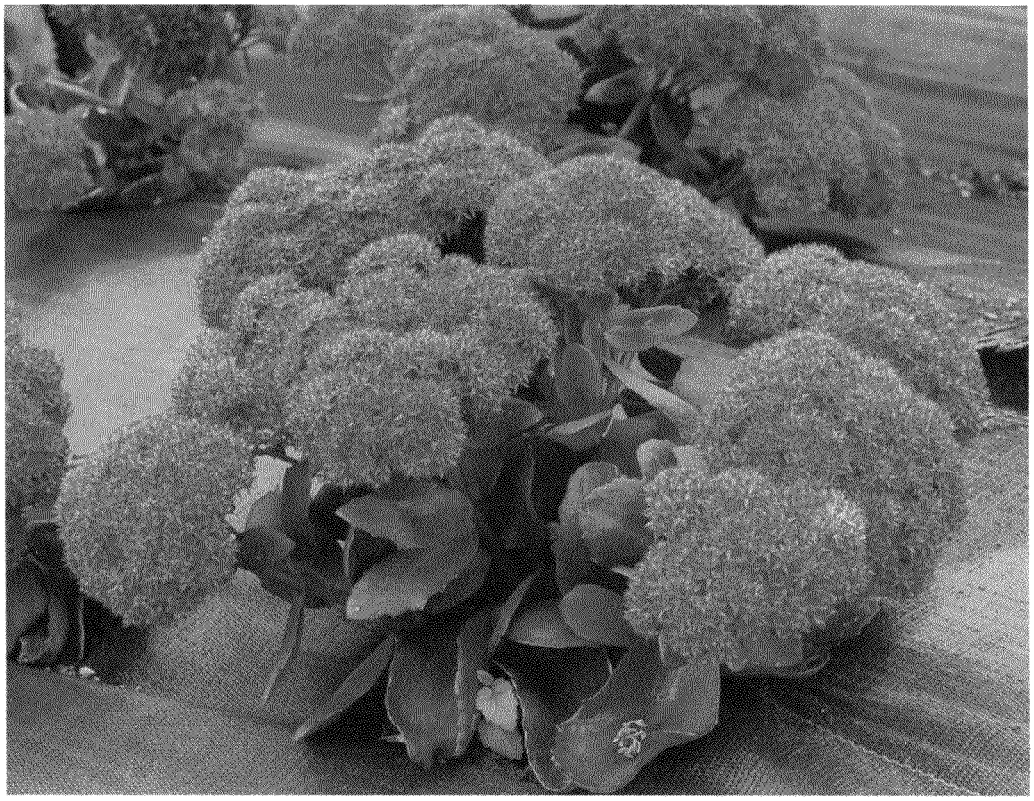

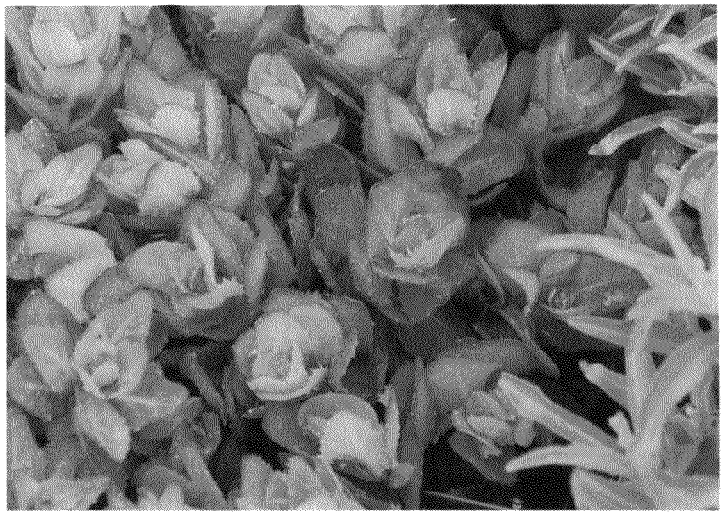
Figure 1 above, Figure 2 below.